United States Patent [19]

Wiedemann et al.

[11] Patent Number: 5,135,912
[45] Date of Patent: Aug. 4, 1992

[54] NATRIURETIC PEPTIDES FROM THE PITUITARY PROHORMONE PROOPIOMELANOCORTIN

[75] Inventors: Eckhart Wiedemann, El Cerrito; Ding Chang, Belmont, both of Calif.

[73] Assignee: Tosoh Corporation, Tokyo, Japan

[21] Appl. No.: 199,816

[22] Filed: May 27, 1988

[51] Int. Cl.$^5$ .......................... C07K 7/06; C07K 7/08; C07K 7/38; A61K 37/40

[52] U.S. Cl. ........................................ 514/13; 514/14; 514/15; 530/326; 530/327; 530/328; 530/306; 930/70

[58] Field of Search ............................ 514/13, 14, 15; 530/326, 327, 328, 306; 930/70

[56] References Cited

U.S. PATENT DOCUMENTS 4,632,780 12/1986 Seidah et al. ...................... 530/306

OTHER PUBLICATIONS

Lymangrover, J. R., et al., *Endocrinology*, 116(3): 1227–1229, 1985.
Lin et al., *Hypertension*, 10(6): 619–627, Dec. 1987.
Lin, S., et al., *Am. J. Physiol.*, 252, F276–F282, Published 1987.
Lin, S., et al., *Am. J. Physiol.*, 249, F282–F290, Published 1985.
Seidah, N., et al., *Adv. Biochem. Psychopharmacol.*, 33, 19–26, published 1982.
Seger, M., et al., *J. Steroid Biochem.*, 25(5B), 703–710, 1986.

*Primary Examiner*—Merrell C. Cashion, Jr.
*Assistant Examiner*—S. M. Perkins
*Attorney, Agent, or Firm*—Nixon & Vanderhye

[57] ABSTRACT

Novel peptides having substantially the amino acid sequence:

X-Gly-Asn-Gly-Asp-Glu-Gln-Pro-Leu-Thr-Y, where X is H, a single amino acid or a short-chain peptide and Y is OH, $NH_2$, a single aminoacid or a short-chain peptide. These peptides have natriuretic and diuretic activity.

10 Claims, 5 Drawing Sheets

FIG. 1

```
        1                                    10
    H-Trp-Cys-Leu-Glu-Ser-Ser-Gln-Cys-Gln-Asp-Leu-Thr
            |                  /                      \
            |                 /                        Thr
        Lys-Cys-Ala-Arg-Ile-Cys-Glu-Leu-Leu-Asn-Ser-Glu
       /
    Pro
       \         30
        Asp-Leu-Ser-Ala-Glu-Thr-Pro-Met-Phe-Pro-Gly-Asn
                                                       \
                                                        Gly
            50                   *                     /
        Tyr-Lys-Arg-Pro-Asn-Glu-Thr-Leu-Pro-Gln-Glu-Asp
       /
    Val
       \
        Met-Gly-His-Phe-Arg-Trp-Asp-Arg-Phe-Gly-Arg-Arg
                                                       \
                                                        *Asn
         76                 70                         /
    OH-Gln-Gly-Ala-Gly-Ser-Ser-Gly-Ser-Ser-Ser-Ser
```

NATRIURETIC PEPTIDES FROM THE PITUITARY PROHORMONE PROOPIOMELANOCORTIN

BACKGROUND OF THE INVENTION

This invention relates to novel peptides possessing potent natriuretic and diuretic activity and sharing sequence homology with portions of the N-terminal fragment (NTF) of the pituitary prohormone proopiomelanocortin (POMC). Similar or identical peptide(s) may function as hormone(s) involved in the physiological regulation of body water and electrolyte balance. In addition, this invention relates to a process for the production of the novel compounds and to pharmaceutical compositions containing said peptides as free acids, as amides or as salts in combination with a pharmaceutically acceptable carrier or diluent, and to the use of such compositions as natriuretic, diuretic or antihypertensive agents in the treatment of congestive heart failure, hypertension and other disturbances of water and electrolyte balance.

POMC, is the precursor molecule of ACTH or corticotropin, the pituitary hormone which regulates production of the glucocorticoid hormone cortisol by the adrenal cortex, as well as of several other biologically active peptides including beta-lipotropin, alpha- and beta-melanotropin, and beta-endorphin. In high concentrations, all of these peptides are capable of stimulating secretion of the mineralocorticoid hormone aldosterone in vitro or in vivo suggesting that they may play a role in the physiological regulation of volume and blood pressure homeostasis, although direct proof for this hypothesis is lacking. While all of these peptides are derived from the mid- and C-terminal portions of the POMC molecule, POMC also contains a large N-terminal fragment of more than 70 aminoacids whose physiological function is still uncertain. Wiedemann ct al. (1982, Program, Seventh Asia and Oceania Congress of Endocrinology, p. 88), synthesized an NTF-midregion peptide, namely NTF[32-49], raised antisera to it and developed a radio-immunoassay suitable to measure NTF midregion-like peptides. Employing this assay to measure NTF midregion-like immunoreactive material (IR-NTF) in plasma in an animal model of natriuresis, the acutely uninephrectomized rat, a consistent positive correlation was observed between the amount of sodium excreted and the plasma concentration of IR-NTF; experimental maneuvers that blocked the rise of IR-NTF also blocked the natriuresis (Lin et al., 1985, Am. J. Physiol. 249, F282; Lin et al., 1987, Am. J. Physiol. 252, F276). These results suggested, but did not prove, promotion of natriuresis by NTF or NTF derived peptides. Neither intact NTF nor peptides derived from the midportion of NTF have previously been shown to affect diuresis or sodium excretion.

We have discovered and now disclose that peptides containing the aminoacid sequence NTF[37-49] possess potent natriuretic and diuretic properties.

SUMMARY OF THE INVENTION

It has been discovered that novel synthetic peptides whose primary structure is

X-Gly-Asn-Gly-Asp-Glu-Gln-Pro-Leu-Thr-Y, where X is H, a single amino acid, e.g. Pro, or a peptide composed of from two to at least six amino acids, e.g. Phe-Pro or Met-Phe-Pro or Val-Phe-Pro or Pro Met-Phe-Pro or Pro-Val-Phe-Pro or Thr-Pro-Met-Phe-Pro or Thr-Pro-Val-Phe-Pro or Glu-Thr-Pro-Met-Phe-Pro or Glu-Thr-Pro-Met-Phe-Pro, and where Y is OH, $NH_2$, a single amino acid, e.g. Glu, or a peptide consisting of from two to at least four amino acids, e.g. Glu-Asn or Glu-Asn-Pro or Glu-Asn-Pro-Arg, and where the C-terminal is the free acid, a salt or an amide, can be used as natriuretic, diuretic and antihypertensive agents.

Therapeutic uses of the invented compounds include, but are not limited to administration to subjects suffering from congestive heart failure and other disorders of volume homeostasis and from hypertension.

DETAILED DESCRIPTION OF THE INVENTION

Structure of the Peptides of this Invention

Figure 1:
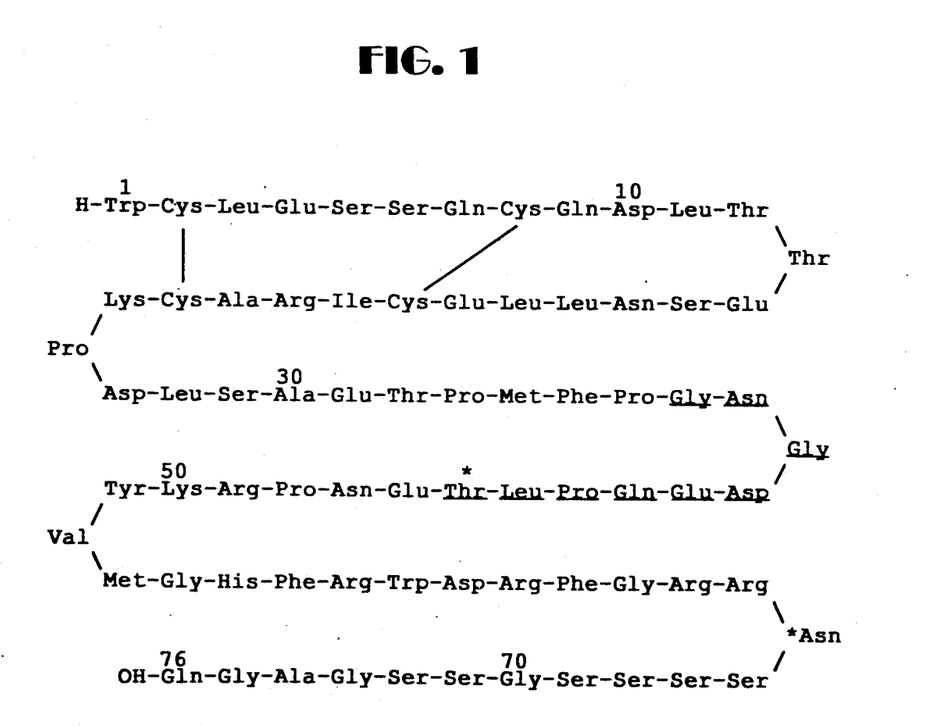
FIG. 1 is a schematic depiction of the amino acid sequence of the human proopiomelanocortin N-terminal fragment. The asterisks indicate sites at which carbohydrate side-chains are attached. The sequence 37–45 is underlined.

All of the inventive peptides contain an active core whose amino acid sequence is identical with the known sequence 37-45 of NTF. However, whereas a carbohydrate side chain is attached to the threonine in position 45 of NTF, some of the peptides of this invention are free of carbohydrate. In FIG. 1, which depicts the primary structure of human NTF, the sequence 37-45 is underlined and the glycosylation sites are marked by asterisks:

Besides the peptide having an amino acid sequence identical to the sequence NTF[37-45], hereinafter also called G9T, this invention includes those peptides having G9T as their core and being N-terminally extended by 1, 2, 3, 4, 5, 6 or more amino acids or C-terminally extended by 1, 2, 3, 4 or more amino acids or both. Both the C-terminal and N-terminal extensions may be either identical with or different from the corresponding amino acids in the naturally occurring sequence of NTF.

Peptide Synthesis

The peptides of this invention can be produced by chemical synthesis employing solid phase or liquid phase methods, by extraction from pituitary glands or other tissues, or by recombinant DNA technology.

Chemical synthesis is preferably carried out by the solid phase method as described by Merrifield (J. Am. Chem. Soc. 85:2148, 1963). With this method protected amino acids bonded to a solid phase resin, such as 4-alkoxybenzyl-resin, are coupled one by one to the growing peptide chain starting with the protected derivative of the amino acid representing the C-terminus of the peptide and employing a complete cycle of deprotection, neutralization and coupling reaction for each successive amino acid. Protection of amino acids is preferably achieved in the following way: the α-amino group in all amino acids is protected with a tert butyloxycarbonyl group (Boc); the B-carboxyl group in aspartic acid and glutamic acid is protected with an O-benzyl group (O-Bzl); the hydroxyl group in serine and threonine is protected with a benzyl group (Bzl); the hydroxyl group in tyrosine is protected with a 2,6-dichlorobenzyl group ($Cl_2Bzl$); the guanidino group in arginine and the imidazole group in histidine are protected with a tosyl group (Tos); the ε-amino group in lysine is protected with a chlorobenzyloxycarbonyl group (Cl-Z) and the thiol group in cysteine is protected with an acetoaminomethyl group (Acm). After completion of synthesis, the protected peptide resin is treated with hydrogen fluoride to remove the peptide from the resin and to remove the protecting groups. The crude peptide is extracted from the peptide-resin mixture with aqueous acetic acid and purified by flash chromatography on C 18 and reverse phase high performance liquid chromatography (HPLC).

The synthetic peptides of this invention can be produced by a skilled investigator with appropriate equipment and the knowledge relevant to the amnio acid sequence of the peptide desired.

The invented compounds can also be produced by extraction of natural POMC N-terminal from pituitary glands, preferably of bovine, porcine or ovine origin, followed by enzymatic cleavage into peptides of the desired structure and extraction and purification of same by standard methods of protein purification. Recombinant DNA technology can also be employed to produce the inventive peptides. For example, oligonucleotides encoding the amino acid sequence of the desired peptide(s) can be synthesized and inserted into a suitable plasmid which is then introduced into E. coli. The peptide then expressed in E. coli is extracted and purified by established methodology.

Bioassays

Diuretic and natriuretic activity of the peptides of this invention is assayed in male rats of the Sprague-Dawley or Long-Evans strains. Peptide or vehicle (for control purposes) is administered by intravenous bolus injection or by continuous infusion into one renal artery of animals anesthetized for the duration of the experiment, or by intramuscular or subcutaneous injection into animals only briefly anesthetized with ether and subsequently conscious and freely moving until completion of the experiment. Timed urine samples are collected for determination of volume and measurement of sodium and potassium concentration by flame photometry. Details of each method are given in Examples II to IV below.

Therapeutic Treatments and Pharmaceutical Presentations

The compounds of this invention are best used for therapeutic purposes in subjects suffering from congestive heart failure or other conditions associated with water and sodium retention, such as chronic renal failure or cirrhosis of the liver, or from hypertension. Compared with conventional diuretic drugs, they offer several advantages. Being peptides, they are readily broken down to natural amino acids which form the building blocks of the body's proteins. Because of their extremely high specific activity they may cause virtually no toxicity and fewer side effects at therapeutic doses than conventional drugs. Compared with other natriuretic peptides, such as the atrial natriuretic peptides, the novel compounds of this invention offer the advantage of a longer duration of action, thereby facilitating less frequent administration.

The novel compounds are useful as active ingredients in diuretic pharmaceutical compositions. They may be used in the form of free acids or as amides or as salts, such as acetate, citrate, hydrochloride, malate, malonate, oxalate or succinate. Parenteral compositions for intravenous, intramuscular or subcutaneous injection may be produced as ready-to-use solutions or as lyophilized powders to be reconstituted in sterile water, saline or other suitable solvent prior to administration. These compositions may contain 0.01 to 100 micrograms of peptide per ml of solution and may also contain inactive ingredients, e.g. buffers such as acetate, bicarbonate or phosphate, antioxidants such as ascorbic acid or tocopherol, preservatives such as butanol, and osmotically active agents such as galactose, glucose, lactose, sorbitol or sucrose. Compositions for parenteral, particularly intramuscular or subcutaneous use, may be specifically formulated for prolonged activity. This may be accomplished by slow release of the active peptides from solid carriers to which they are adsorbed, e.g. zinc hydroxide, or from viscous liquids in which they are dissolved, e.g. oils or partially hydrogenated gelatin, or from hydrocolloids in which they are suspended, e.g. sodium alginate, sodium carboxymethyl-cellulose or polyvinyl-pyrrolidone, or from liposomes in which they are microencapsulated. Pharmaceutical compositions may also be formulated as rectal suppositories, nasal sprays, sublingual tablets or transdermal skin patches. Pharmaceutical presentations that protect the peptides from the digestive enzymes of the stomach and small intestine may also be considered. The absolute quantity of active ingredients present in any dosage unit should not exceed that appropriate to the rate and manner of administration to be employed, but on the other hand, should also desirably be adequate to allow the desired rate of administration to be achieved by a small number of doses.

The preferred, but not exclusive route of administration is the parenteral one, namely intravenous, intramuscular or subcutaneous injection. The appropriate dose range is from 0.002 to 20.0, but preferably from 0.02 to 2.0 nanomoles peptide per kg body weight. However, the dose to be administered in any given case as well as the rate of administration will depend on the specific peptide used, the pharmaceutical formulation employed, the specific purpose of administration and such factors as age, sex and coexisting diseases.

EXAMPLE I

The peptide Phe-Pro-Gly-Asn-Gly-Asp-Glu-Gln-Pro-Leu-Thr-Glu-Asn-Pro-Arg-OH, hereinafter referred to as F15R, was synthesized according to the Solid Phase Peptide Synthesis Method described above. Starting with Boc-Arg(Tos)-O-resin (0.38 meq/g substitution) as the C-terminal residue, 14 successive cycles of deprotection, neutralization and coupling reaction were performed in the following order: Boc-Pro, Boc-Asn, Boc-Glu(OBzl), Boc-Thr(Bzl), Boc-Leu, Boc-Pro, Boc-Gln, Boc-Glu(OBzl), Boc-Asp(OBzl), Boc-Gly, Boc-Asn, Boc-Gly, Boc-Pro and Boc-Phe. The following scheme was used to couple each new amino acid to the growing peptide chain:

2.6 g of the Boc-Arg(Tos)-O-resin was washed three times with methylene chloride (MeCl). The Boc-group was then removed by treatment with 40% TFA in MeCl (v:v), employing a 5-minute prewash followed by 30 minutes deprotection reaction. The amino acid resin was washed three times with MeCl and twice with ethanol (EtOH) and was then neutralized with 10% triethylamine in MeCl employing a 5-minute prewash followed by 10 minutes neutralization. After washing the resin three times with MeCl, the coupling reaction was carried out. Except for incorporation of $Asn^4$, $Gln^8$, and $Asn^{13}$, coupling was performed as follows: A three fold excess (6 mmole) of the appropriate Boc-amino acid in 25 ml MeCl was added to the deprotected peptide-resin. After stirring for 2 minutes, a three-fold excess of dicyclohexyl-carbodiimide (DCC) (6 mmole) in 15 ml of MeCl was added and was allowed to react for two hours. $Asn^4$, $Gln^8$ and $Asn^{13}$ were incorporated by the DCC and hydroxybenzotriazole (HOBT) method using a six fold excess of HOBT and a sixfold excess of DCC in a mixture of dimethylformamide and MeCl (1:1). In all cases, the peptide-resin was washed three times with MeCl, twice with EtOH and three times with MeCl following the coupling reaction. Completeness of the coupling; reactions was monitored by the ninhydrin color test procedure of Kaiser et al. (Anal. Biochem. 34:595-598; 1970). After completion of the synthesis, the protected peptide-resin was washed with MeCl, the treated with 40% TFA in MeCl for 30 minutes, then washed successively with MeCl, EtOH and MeCl and dried under vacuum. The dried peptide-resin weighed 4.0 g. Deprotection and cleavage of the peptide was effected with 70 ml of distilled anhydrous hydrogen fluoride (HF) in the presence of 7.5 ml anisole for 30 minutes at $-20°$ C. and 30 minutes at $0°$ C. After removal of the excess HF, the peptide-resin mixture was washed with anhydrous ether to remove anisole and its derivatives. The crude peptide was extracted with 10% aqueous acetic acid. The crude lyphilized product (1.1 g) was purified by flash chromatography on a 4×20 cm column of C-18 (J. T. Baker, 40 micron), employing a 0 to 100% B linear gradient (A: 1 liter 0.1% TFA; B: 1 liter 30% acetonitrile/70% $H_2O$) at a flow rate of 2.5 ml/minute. The eluate was monitored at 254 nm and analyzed by analytical HPLC and thin-layer chromatography (TLC). This procedure was repeated twice to give a total of 47.1 mg of final peptide product. This peptide was analyzed by HPLC, TLC, paper electrophoresis, amino acid analysis and high performance electrophoresis and found to be substantially free of impurities (Table I).

The peptides G9T, G13R and E19R, having the amino acid sequences Gly-Asn-Gly-Asp-Glu-Gln-Pro-Leu-Thr, Gly-Asn-Gly-Asp-Glu-Gln-Pro-Leu-Thr-Pro-Asn-Pro-Arg and Glu-Thr-Pro-Met-Phe-Pro-Gly-Asn-Gly-Asp-Glu-Gln-Pro-Leu-Thr-Glu-Asn-Pro-Arg, respectively, were synthesized and analyzed by the same methods as F15R. Amino acid analysis and TLC data for these peptides are listed in Table II and Table III, respectively.

TABLE I
Analysis of Synthetic Peptide F15R.

A. Thin Layer Chromatography:

| | |
|---|---|
| Cellulose F: | nBuOH:Pyr:HOAc:$H_2O$, 15:10:3:12. Ninhydrin. |
| | Result: Main spot with a negligible upper and lower spots. $R_f = 0.34$ |
| Cellulose $F_c$: | nBuOH:Pyr:HOAc:$H_2O$, 21:12:2:15. Ninhydrin. |
| | Result: Main spot with a negligible upper and lower spots. $R_f = 0.58$ |

B. Paper Electrophoresis:

Whatman 3 MM, pH 1.9 (HCOOH:Acet.); 1,000 V, 1 hr. Ninhydrin.
Result: Main spot traveling towrds the cathode with a negligible lower spot. $R_f = 0.42$ with reference to arginine.

C. Amino Acid Analysis:

Percent Peptide: 84.6

| | Theory | Found |
|---|---|---|
| Asp | 3 | 2.95 |
| Thr | 1 | 1.02 |
| Glu | 3 | 3.07 |
| Pro | 3 | 2.91 |
| Gly | 2 | 2.12 |
| Leu | 1 | 0.99 |
| Phe | 1 | 0.99 |
| NH | 3 | 2.71 |
| Arg | 1 | 0.87 |

D. High Performance Liquid Chromatography:

HPLC Model Perkin-Elmer. C-18 column. Flow 1.0 ml/min.
Solvent A: 0.05 M $NaH_2PO_4$; Solvent B: 60% $CH_2CN$ in A.
Gradient: Linear 0 to 100% B in 40 min. Recorder 1.0 mm/min. Detector: 210 nm. Sample: 0.15 μl of 0.16 mg in 200 μl of A.
Result: Single peak. Retention time 15.99 min.

E. High Performance Electrophoresis:

8,000 V/30 cm, 15 μA, 25 μm ID, 0.2 M phosphate buffer, pH 2.56. Detector: 200 nm. Recorder: 1 scale/min from + to −. Running time; 40 min.
Result: No slow migrating components in sample.

TABLE II
Amino Acid Analysis of Peptides G9T, G13R and E19R.

| | G9T | | G13R | | E19R | |
|---|---|---|---|---|---|---|
| | Theory | Found | Theory | Found | Theory | Found |
| Arg | — | — | 1 | 0.88 | 1 | 1.13 |
| Asp | 2 | 1.89 | 3 | 3.02 | 3 | 2.94 |
| Glu | — | — | 3 | 3.07 | 4 | 4.31 |
| Gly | 2 | 1.95 | 2 | 2.07 | 2 | 1.86 |
| Leu | 1 | 1.07 | 1 | 1.04 | 1 | 1.06 |
| Met | — | — | — | — | 1 | 0.95 |
| Ph3 | — | — | — | — | 1 | 0.96 |
| Pro | 1 | 1.01 | 2 | 1.99 | 4 | 3.77 |
| Thr | 1 | 0.92 | 1 | 1.03 | 2 | 1.74 |
| $NH_2$ | 2 | 2.16 | 3 | 3.03 | 3 | 3.26 |

TABLE III
Thin Layer Chromatography of Peptides G9T, G13R and E19R.

| | | $R_f$ | | |
|---|---|---|---|---|
| | | G9T | G13R | E19R |
| Silica $F_m$ | nBuOH:Pyr:HOAc:$H_2O$, 15:15:3:12) | 0.30 | 0.17 | — |
| Silica | (nBuOH:EtOAc:HOAc:$H_2O$, 1:1:1:1) | 0.24 | — | — |
| Cellulose F | (nBuOH:Pyr:HOAc:$H_2O$, 15:10:3:12) | — | 0.14 | 0.29 |
| Cellulose $F_c$ | (nBuOH:Pyr:HOAc:$H_2O$, 21:12:2:15) | — | 0.06 | |
| Cellulose $F_c$ | (nBuOH:Pyr:HOAc:$H_2O$, 42:24:4:30) | — | — | 0.28 |

EXAMPLE II

Figure 2:
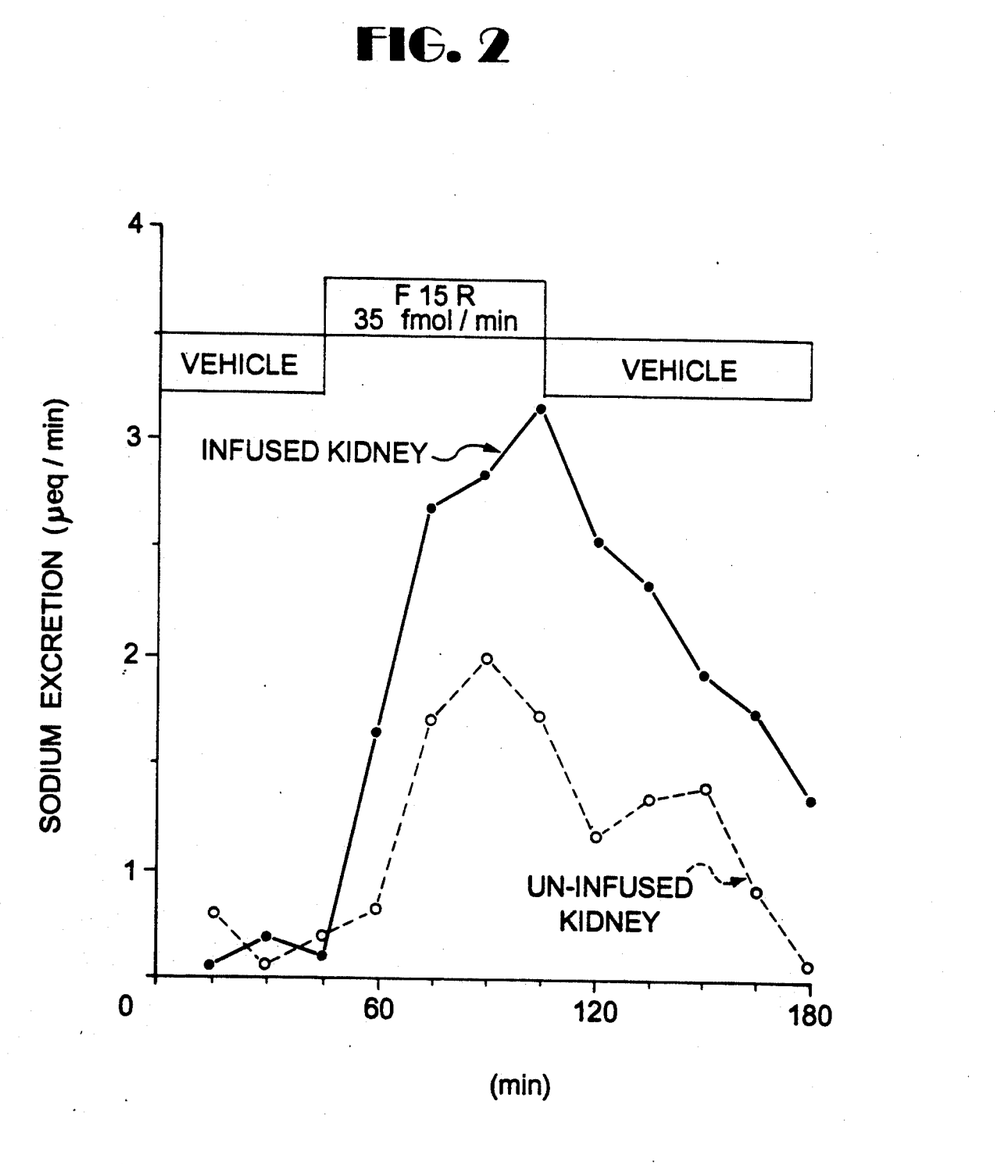
FIG. 2 is a graph plotting urinary sodium excretion against time for the sequential infusion of vehicle/peptide F15R/vehicle into the left renal artery of a rat as described in more detail in Example II that follows.

The natriurotic and diuretic activity of the inventive peptides F15R, G13R, E19R and G9T was assessed by intrarenal infusion in rats. FIG. 2 shows a typical example of the effect of intrarenal infusion of F15R on sodium excretion by the infused and the uninfused kidney. A 350 gram male Sprague-Dawley rat was given an intraperitoneal injection of 42 mg of the long-acting barbiturate Inactin® (Byk-Gulden, Konstanz, FRG) under light ether anesthesia.

Figure 3:
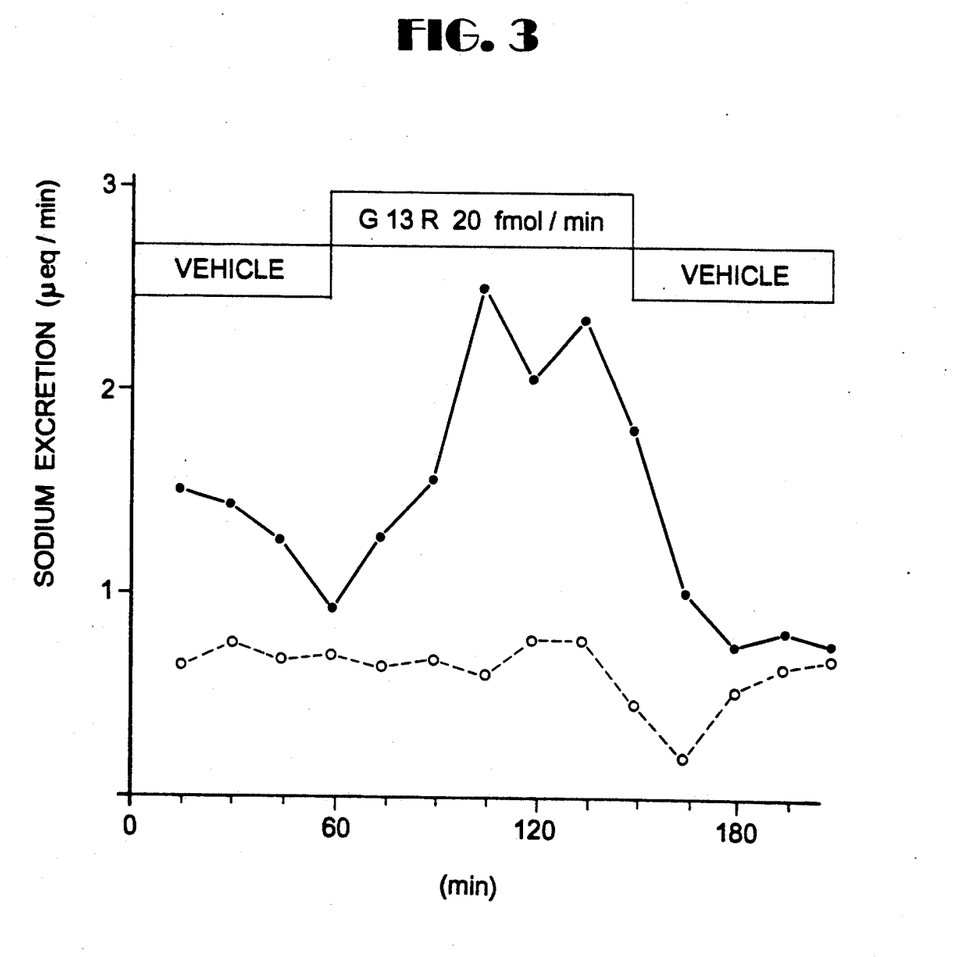
FIG. 3 is a graph plotting urinary sodium excretion against time for the sequential infusion of vehicle/peptide G13R/vehicle into the left renal artery of a rat as described in more detail in Example II that follows.
Figure 4:
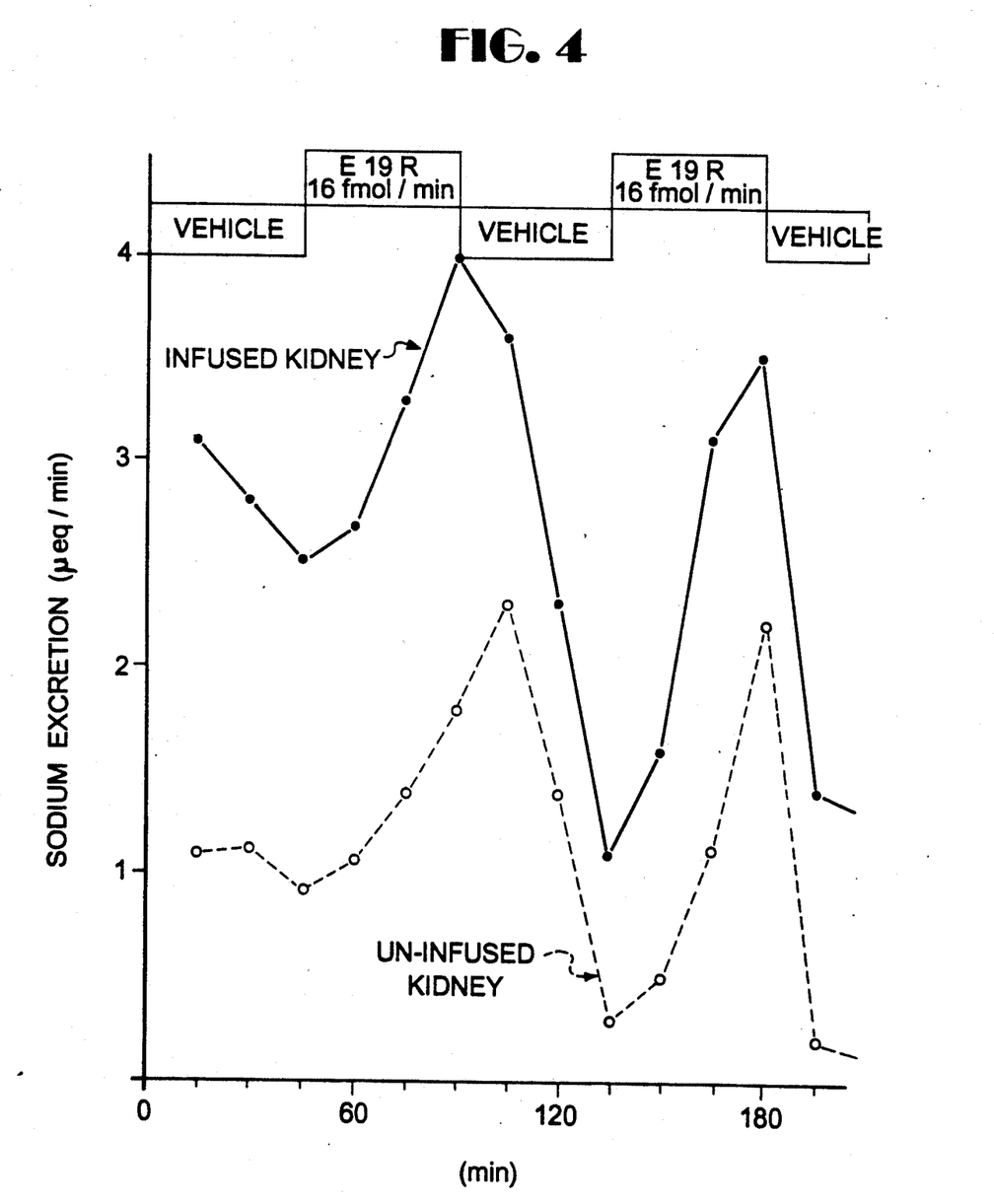
FIG. 4 is a graph plotting urinary sodium excretion against time for the sequential infusion of vehicle/peptide E19R/vehicle/peptide E19R into the left renal artery of a rat as described in more detail in Example II that follows.
Figure 5:
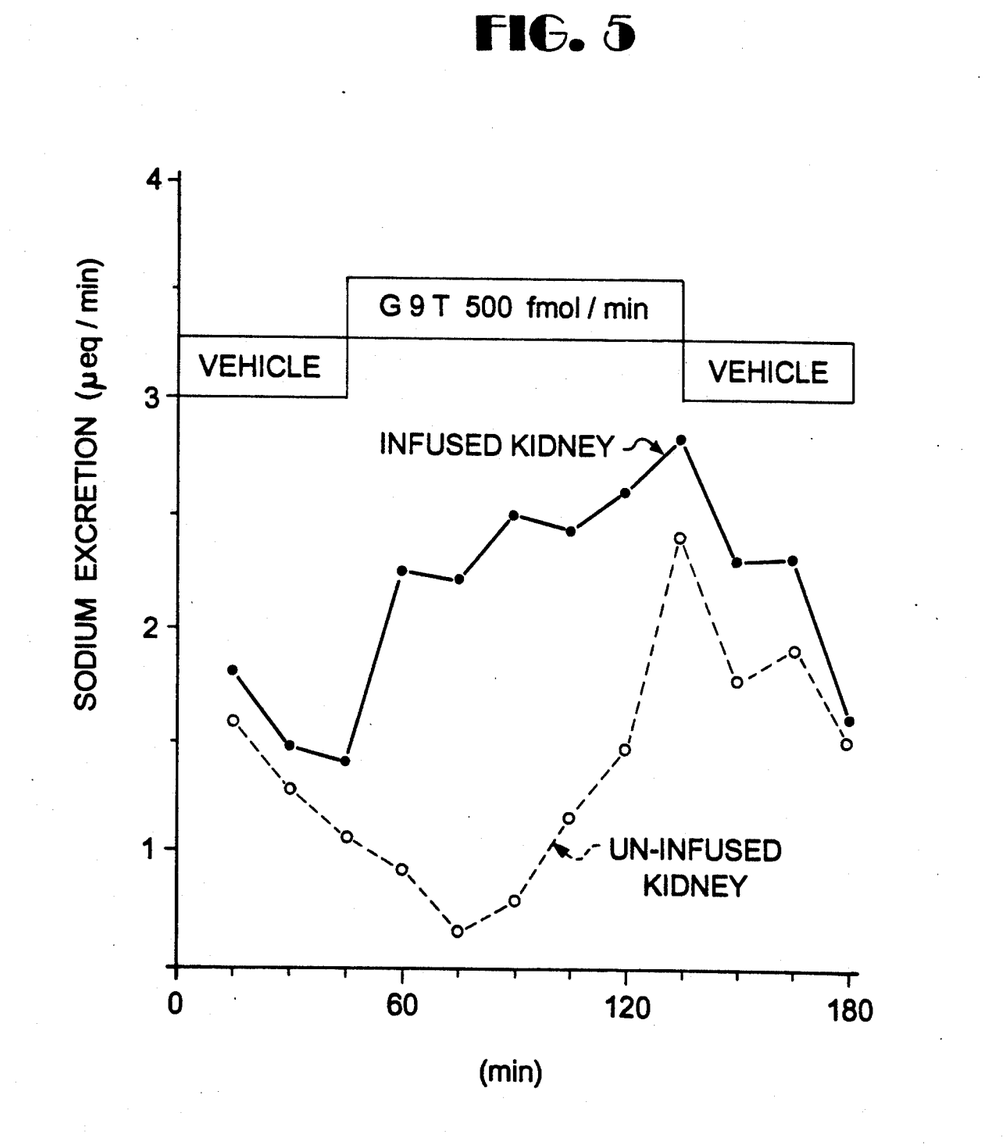
FIG. 5 is a graph plotting urinary sodium excretion against time for the sequential infusion of vehicle/peptide G9T/vehicle into the left renal artery of a rat as described in more detail in Example II that follows.

After placement of a tracheal cannula, a catheter was placed in the right femoral vein for infusion of 5.25 ml of 5% bovine serum albumin in saline over a period of 30 minutes, followed by saline at a rate of 2.0 ml/hour for the duration of the experiment. Through a midline abdominal incision the left kidney was exposed, a catheter was placed in the left ureter for urine collections, and a 30 gauge needle attached to a catheter was inserted into the left renal artery for infusion of vehicle (1% bovine serum albumin and 0.1% bacitracin in normal saline) at a rate of 1.0 ml/hour. Surgical preparation was completed within 45 minutes by closure of the abdominal incision. After a recovery period of 60 minutes, serial 15-minute urine collections from the left and right kidney were begun using preweighed vials. Following three control periods, the vehicle infusion was replaced by F15R infusion (1.8 pmol/ml) at the identical flow rate, resulting in the delivery of 30 fmol F15R per minute into the left renal artery. After 60 minutes, the intrarenal infusion was switched back to vehicle for another 75 minutes. Urine volumes were determined by weight and urine sodium and potassium concentrations were measured by flame photometry. As shown in FIG. 2, F15R produced an immediate increase in sodium excretion from the infused kidney, reaching a peak rate five times the basal rate after one hour and followed by a prompt decline after cessation of the F15R infusion. Qualitatively similar, but smaller changes occurred also in the un infused kidney due to spill-over of F15R into the general circulation. Intrarenal infusion of peptides G13R, E19R and G9T evoked similar natriuretic responses as F15R as shown in FIGS. 3, 4 and 5, respectively.

EXAMPLE III

The natriuretic and diuretic effect of intravenous bolus injection of peptides F15R, G13R and E19R was tested in male Sprague-Dawley or Long-Evans rats weighing 300–400 g. The animals were given Inactin®, 120 mg per kg body weight i.p. under light ether anesthesia. Following placement of a tracheal cannula, the right femoral vein was catheterized for infusion of 5% bovine serum albumin at a dose of 0.4% of body weight and at a rate of 6.0 ml/hour. Subsequently, normal saline was infused for the duration of the experiment at a rate of 2.0 ml/hour. The bladder was exposed through an abdominal incision and catheterized for urine collection. Serial 15-minute urine collections in preweighed vials were begun after a recovery period of 45 minutes. After collection of four control samples, the peptide in 0.1 ml of vehicle was injected into the femoral vein over a period of 1 minute and 6 to 10 further urine samples were collected. Urine volume was determined by weighing and urine sodium and potassium were assayed by flame photometry. All peptides produced natriuresis and diuresis reaching peak levels usually between 30 and 60 minutes after injection. The difference between urine volume and sodium excretion observed from 30 to 60 minutes after and 30 to 0 minutes before peptide administration was calculated for each rat as a measure of activity. The results are shown in Table IV below.

TABLE IV

Effects of Intravenous Injection of F15R, G13R and E19R*.

| Treatment | | | No. of Rats | Change in Urine Volume μl/30 minutes | Change in Sodium Excretion μeq/30 minutes |
|---|---|---|---|---|---|
| Vehicle | | | 25 | 91.4 ± 36.8 | 0.59 ± 0.97 |
| F15R | 0.025 | nmol | 6 | 111.2 ± 20.2 | 25.75 ± 12.02 |
| | 0.100 | nmol | 9 | 306.6 ± 101.6 | 45.43 ± 19.34 |
| G13R | 0.10 | nmol | 5 | 80.0 ± 29.2 | 8.39 ± 4.41 |
| | 1.00 | nmol | 6 | 62.0 ± 17.2 | 12.48 ± 6.22 |
| E19R | 0.025 | nmol | 8 | 89.0 ± 43.6 | 6.50 ± 3.60 |
| | 0.100 | nmol | 7 | 104.2 ± 58.0 | 12.07 ± 5.08 |

*Values represent mean ± SEM

EXAMPLE IV

The effectiveness of subcutaneous administration of peptide F15R was demonstrated in conscious, freely moving rats. Under light ether anesthesia, six male Long-Evans rats weighing 320 to 400 g were given an intraperitoneal load of sterile saline equivalent to 2.5% of body weight and a subcutaneous injection of 0.1 ml of either vehicle (1% bovine serum albumin and 0.1% bacitracin in saline) or F15R (0.25 nmoles/kg body weight). They were then placed individually in metabolic cages without food or water. The urine spontaneously voided during the following six hours was collected separately after each micturition. Urine volumes were determined by weight and urine sodium and potassium concentrations were measured by flame photometry. On the following day, the experiment was repeated in the same manner except that the animals that had received vehicle were given peptide and vice versa. As shown in Table V below, F15R administration increased urine volume, sodium excretion and the urinary Na/K ratio.

TABLE V

Effect of Subcutaneous Administration of F15R*.

| | Vehicle | F15R |
|---|---|---|
| Urine volume (ml/6 hours) | 8.04 ± 0.76 | 10.69 ± 0.47 |
| Sodium excretion (μeq/6 hours) | 906 ± 95 | 1,330 ± 148 |
| Urinary Na/K ratio | 1.97 ± 0.16 | 2.80 ± 0.42 |

*Values represent mean ± SEM

What is claimed is:

1. A peptide having the amino acid sequence:

X-Gly-Asn-Gly-Asp-Glu-Gln-Pro-Leu-Thr-Y, where
X is as follows:
 H, or
 Pro, or
 Phe-Pro, or
 Met-Phe-Pro, or
 Pro-Met-Phe-Pro, or
 Glu-Thr-Pro-Met-Phe-Pro;
and
Y is as follows:
 OH, or
 Glu, or
 Glu-Asn, or
 Glu-Asn-Pro, or
 Glu-Asn-Pro-Arg, or Glu-Asn-Pro-Arg-NH₂

2. A method of causing natriuresis, diuresis or both in a patient comprising administering to said patient a natriuretically or diuretically effective amount of a peptide of claim 1.

3. A method of treating the sodium and water retention of congestive heart failure, of liver cirrhosis and of the nephrotic syndrome in a patient comprising administering to said patient an effective amount of a peptide of claim 1.

4. A method of treating hypertension in a patient comprising administering to said patient a hypertension reducing amount of a peptide of claim 1.

5. The method of claim 2, 3 or 4 in which the peptide is administered in an amount of from about 0.002 to about 20.0 nanomoles per kg body weight per day.

6. A natriuretic or diuretic pharmaceutical composition comprising a therapeutically effective amount of a peptide of claim 1 together with a pharmaceutically acceptable carrier or diluent.

7. The pharmaceutical composition of claim 6 in which the peptide is present in an amount of from about 0.001 to 0.1 mg.

8. A method of causing natriuresis in a patient comprising administering to said patient a natriuretically-effective amount of the peptide:

Thr-Pro-Met-Phe-Pro-Gly-Asn-Gly-Asp-Glu-Gln-Pro-Leu-Thr-Glu-Asn-Pro-Arg or an amide thereof.

9. A method of treating sodium and water retention of congestive heart failure, of liver cirrhosis and of the nephrotic syndrome in a patient comprising administering to said patient an effective amount of the peptide Thr-Pro-Met-Phe-Pro-Gly-Asn-Gly-Asp-Glu-Gln-Pro-Leu-Thr-Glu-Asn-Pro-Arg or an amide thereof.

10. A method of treating hypertension in a patient comprising administering to said patient a hypertension-reducing amount of the peptide Thr-Pro-Met-Phe-Pro-Gly-Asn-Gly-Asp-Glu-Gln-Pro-Leu-Thr-Glu-Asn-Pro-Arg or an amide thereof.

* * * * *